(12) United States Patent
Suwa (10) Patent No.: US 12,035,886 B2
(45) Date of Patent: Jul. 16, 2024

(54) ENDOSCOPE, INSERTION PORTION AND DISTAL-END CONSTITUTING PORTION FOR USE WITH ENDOSCOPE

(71) Applicant: OLYMPUS MEDICAL SYSTEMS CORP., Tokyo (JP)

(72) Inventor: Takahiro Suwa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 17/592,709

(22) Filed: Feb. 4, 2022

(65) Prior Publication Data

US 2023/0248223 A1 Aug. 10, 2023

(51) Int. Cl.
*A61B 1/00* (2006.01)
*A61B 1/12* (2006.01)

(52) U.S. Cl.
CPC .......... *A61B 1/00179* (2013.01); *A61B 1/126* (2013.01)

(58) Field of Classification Search
CPC ..... A61B 1/00179; A61B 1/015; A61B 1/126; A61B 1/0008; A61B 1/00174
See application file for complete search history.

(56) References Cited

U.S. PATENT DOCUMENTS

| 4,846,154 | A | * | 7/1989 | MacAnally | ........ | A61B 1/00165 |
| | | | | | | 349/1 |
| 5,305,736 | A | * | 4/1994 | Ito | ........................ | A61B 1/0008 |
| | | | | | | 600/176 |
| 5,386,817 | A | * | 2/1995 | Jones | .................. | A61B 1/00135 |
| | | | | | | 600/125 |
| 5,518,502 | A | * | 5/1996 | Kaplan | ................... | A61B 1/127 |
| | | | | | | 600/156 |
| 5,630,795 | A | * | 5/1997 | Kuramoto | .............. | A61B 1/126 |
| | | | | | | 600/156 |
| 6,149,598 | A | * | 11/2000 | Tanaka | ...................... | A61B 8/12 |
| | | | | | | 600/437 |
| 2009/0043166 | A1 | * | 2/2009 | Ishii | .................... | A61B 1/00179 |
| | | | | | | 600/130 |
| 2015/0250377 | A1 | * | 9/2015 | Iizuka | ................ | A61B 1/00045 |
| | | | | | | 600/103 |

FOREIGN PATENT DOCUMENTS

| JP | 2016-202707 A | 12/2016 |
| JP | 2018-134308 A | 8/2018 |
| WO | 2014/030385 A1 | 2/2014 |

\* cited by examiner

*Primary Examiner* — Aaron B Fairchild
(74) *Attorney, Agent, or Firm* — Scully, Scott, Murphy & Presser, P.C.

(57) ABSTRACT

An endoscope includes: a distal-end constituting portion provided at a distal end of an insertion portion of the endoscope; an observation window having a field of view direction that intersects a longitudinal axis of the insertion portion; a first flat surface on which the observation window is arranged, the first flat surface constituting a part of a surface of the distal-end constituting portion and having a first intersection angle with respect to the longitudinal axis; a second flat surface constituting a part of the surface of the distal-end constituting portion, the second flat surface being provided on a distal end side or a proximal end side with respect to the first flat surface, and having a second intersection angle with respect to the longitudinal axis, the second intersection angle being smaller than the first intersection angle; and a supply unit arranged on the second flat surface.

19 Claims, 5 Drawing Sheets

ENDOSCOPE, INSERTION PORTION AND DISTAL-END CONSTITUTING PORTION FOR USE WITH ENDOSCOPE

BACKGROUND OF THE INVENTION

1. Field of the Invention

The present invention relates to a shape of a distal-end constituting portion of an endoscope, and an arrangement configuration of a plurality of constituting units disposed in the distal-end constituting portion.

2. Description of the Related Art

Conventionally, ultrasound endoscope systems have been put into practical use, and such ultrasound endoscope systems are capable of searching for and observing a lesion part in a body cavity based on an observation image obtained by an image pickup device and displayed on a display screen, and also capable of performing various kinds of treatment, such as sucking and collecting of living tissues, cells, and the like of the lesion part by puncturing a puncture needle into the lesion part while observing the lesion part by using an ultrasound image.

An endoscope included in a conventional endoscope system of the above-described type includes various constituting units in a distal-end constituting portion provided at a distal end of an insertion portion. For example, in the distal-end constituting portion, a plurality of constituting units such as an image pickup unit, an illumination unit, a gas/liquid feeding unit, and the like are disposed. Members disposed at the respective distal ends of these respective constituting units are generally arranged on a surface (a distal end surface, in particular) of the distal-end constituting portion.

The distal end surface of the distal-end constituting portion indicates a surface which constitutes a part of the surface of the distal-end constituting portion and which is formed so as to face a region in front of the distal-end constituting portion. On the distal end surface of the distal-end constituting portion, specifically, for example, an observation window located at the distal end of the image pickup unit, an illumination window located at the distal end of the illumination unit, a fluid supply nozzle located at the distal end of the gas/liquid feeding unit, and the like are disposed.

Some of conventional ultrasound endoscopes include an ultrasound probe at a position on a distal-most side of a distal-end constituting portion. Therefore, such a type of conventional ultrasound endoscopes require an ingenuity for preventing the ultrasound probe from being reflected on an observation screen of an image pickup unit.

The endoscope disclosed by Japanese Patent Application Laid-Open Publication No. 2018-134308, for example, is configured such that a field of view direction of the image pickup device is directed in the front diagonal direction. Such a type of endoscope, what is called an oblique-viewing endoscope, includes a distal-end constituting portion having a distal end surface formed by a plane which is inclined with respect to the insertion axis.

SUMMARY OF THE INVENTION

An endoscope according to one aspect of the present invention includes: a distal-end constituting portion provided at a distal end of an insertion portion of the endoscope; an observation window having a field of view direction that intersects a longitudinal axis of the insertion portion; a first flat surface on which the observation window is arranged, the first flat surface constituting a part of a surface of the distal-end constituting portion, the first flat surface having a first intersection angle with respect to the longitudinal axis; a second flat surface constituting a part of the surface of the distal-end constituting portion, the second flat surface being provided on a distal end side or a proximal end side with respect to the first flat surface, the second flat surface having a second intersection angle with respect to the longitudinal axis, the second intersection angle being smaller than the first intersection angle; and a supply unit arranged on the second flat surface.

A distal-end constituting portion of an endoscope according to one aspect of the present invention includes: a base member; an observation window having a field of view direction that intersects a longitudinal axis of the base member; a first flat surface on which the observation window is arranged, the first flat surface constituting a part of a surface of the base member, the first flat surface having a first intersection angle with respect to the longitudinal axis; a second flat surface constituting a part of the surface of the base member, the second flat surface being provided on a distal end side or a proximal end side with respect to the first flat surface, the second flat surface having a second intersection angle with respect to the longitudinal axis, the second intersection angle being smaller than the first intersection angle; and a supply unit arranged on the second flat surface.

DETAILED DESCRIPTION OF THE PREFERRED EMBODIMENTS

In general, it is known that, the closer to a configuration (what is called, a front-viewing configuration), the more excellent an insertion operability of an endoscope. In the front-viewing configuration, a field of view direction of an image pickup unit substantially coincides with a direction of an insertion axis of the insertion portion of the endoscope. In addition, an endoscope has such an advantage that the closer to the front-viewing configuration, the more accurately the endoscope can capture an observation region in front of the endoscope.

Therefore, also in an oblique-viewing endoscope, there is a desire for achieving a configuration in which a field of view direction of an image pickup unit is made to coincide as much as possible with a direction of an insertion axis of an insertion portion in order to ensure an improvement of the insertion performance of the insertion portion and an accurate observation field of view.

However, in a case where the oblique-viewing endoscope is configured so as to be close to the configuration in which the field of view direction of the image pickup unit is made to coincide with the direction of the insertion axis of the insertion portion, the area of the inclined face of the distal end surface tends to be narrow. If the area of the inclined face of the distal end surface of the distal-end constituting portion becomes narrow, it would be difficult to achieve effective and efficient arrangement of various constituting members (observation window, illumination window, fluid supply nozzle, etc.) that are arranged on the distal end surface.

The present invention, which is described below, can provide an endoscope and a distal-end constituting portion of the endoscope, which are capable of achieving effective and efficient arrangement of various constituting members (observation window, illumination window, fluid supply nozzle, etc.) that are arranged on a distal end surface of a distal-end constituting portion, while ensuring an improvement of an insertion performance of an insertion portion and an accurate observation field of view.

Hereinafter, the present invention will be described by illustrated embodiments. The drawings used in the following description are schematically shown, and in order to show each constituent element in a size recognizable on the drawings, there is a case where respective members are shown so that the dimensional relationship, scales, etc., of the respective members are made different among respective constituent elements. Therefore, the present invention is not limited only to the illustrated forms with respect to the number, the shapes, the ratio of the sizes, the relative positional relationship, and the like of the respective constituent elements described in the respective drawings.

Figure 1:
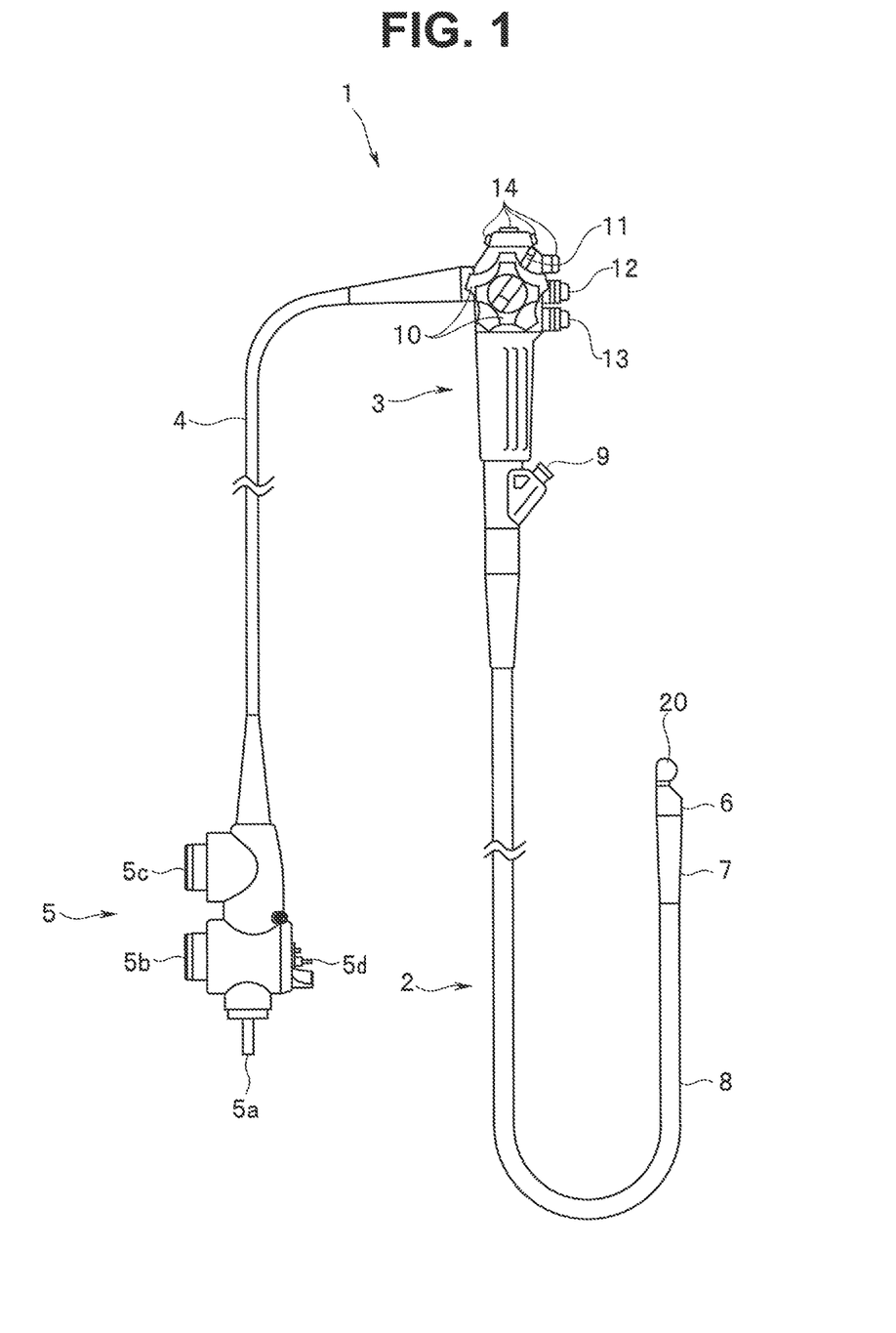
FIG. 1 is a schematic view showing an overall configuration of an endoscope according to a first embodiment of the present invention.

First, description will be made on an overall configuration of an endoscope according to a first embodiment of the present invention with reference to FIG. 1. FIG. 1 is a schematic view showing the overall configuration of the endoscope according to the first embodiment of the present invention.

An endoscope 1 shown in FIG. 1 is an example of an oblique-viewing ultrasound endoscope capable of obtaining an observation image in a subject by an image pickup unit as well as an ultrasound tomographic image by ultrasonically scanning a desired observation site (where a lesion part and the like exist) in the subject.

The endoscope 1 mainly includes an insertion portion 2, an operation portion 3, a universal cord 4, an endoscope connector 5, an ultrasound probe 20, etc.

The ultrasound probe 20 is a constituting unit for obtaining an ultrasound tomographic image. The ultrasound probe 20 is disposed at a distal end part of a distal-end constituting portion 6 provided at the distal end of the insertion portion 2. The ultrasound probe 20 includes a plurality of ultrasound transducers and is configured to transmit and receive ultrasounds. The ultrasound probe 20 itself is assumed to have a general configuration applied to a conventional ultrasound endoscope, and detailed description on the configuration thereof will be omitted.

A balloon is provided around the ultrasound probe 20 so as to cover the ultrasound probe 20, although illustration thereof is omitted. The inside of the balloon is filled with an ultrasound medium. The ultrasound medium is provided for an efficient transfer of ultrasounds between the ultrasound probe 20 and an ultrasound observation object site when ultrasound scanning for obtaining an ultrasound tomographic image is performed by using the ultrasound probe 20.

The insertion portion 2 is a constituting member formed in an elongated tubular shape and configured to be inserted into a lumen of a subject. The insertion portion 2 includes the distal-end constituting portion 6, a bending portion 7, and a flexible tube portion 8. The distal-end constituting portion 6, the bending portion 7, and the flexible tube portion 8 are linked to each other in this order from the distal end side of the insertion portion 2.

The distal-end constituting portion 6 is arranged at the distal end of the insertion portion 2. The distal-end constituting portion 6 includes a base member 6a (see FIG. 2, etc.), various constituting units, and the like. The base member 6a is made of a rigid member and has inside thereof a predetermined space. The various constituting units are disposed respectively at predetermined positions in the space inside the base member 6a. The distal-end constituting portion 6, includes inside thereof, for example, an image pickup unit 21, an illumination unit, a gas/liquid feeding unit 23, and the like (not shown in FIG. 1, see FIG. 2, FIG. 3 to be described later, etc.) that are described later.

The bending portion 7 is a constituting unit configured to be bendable. The bending portion 7 is assumed to have a general configuration to be applied to a conventional endoscope, and detailed description on the configuration thereof will be omitted.

The flexible tube portion 8 is a constituting member having flexibility and formed in a long tubular shape. Inside the flexible tube portion 8, not only cables, not shown, but also a gas/liquid feeding conduit 23c of the gas/liquid feeding unit 23 (not shown in FIG. 1, see FIG. 2, etc., to be described later), a treatment instrument insertion channel, not shown, and the like are inserted through. The not-shown cables (an image pickup signal line, an image pickup control signal line, an optical fiber cable or an illumination signal line, an ultrasound connection line, etc.) are extended from the respective constituting units (the image pickup unit 21, the illumination unit, the ultrasound probe 20, etc.) provided in the distal-end constituting portion 6.

The operation portion 3 is a constituting unit provided so as to be continuous with the proximal end side of the insertion portion 2. The operation portion 3 includes a treatment instrument insertion port 9, a bending operation knob 10, a treatment instrument raising lever 11, a suction button 12, a gas/liquid feeding button 13, a plurality of remote switches 14, and the like.

The treatment instrument insertion port 9 is an opening portion through which a treatment instrument, not shown, is inserted. The treatment instrument insertion port 9 communicates with the treatment instrument insertion channel, not shown, inserted through the inside of the insertion portion 2.

The bending operation knob 10 is an operation member for operating the bending of the bending portion 7. The drawings show one example in which the bending operation knob 10 is a rotary operation member.

The treatment instrument raising lever 11 is an operation member for changing the protruding direction of the treatment instrument (not shown) which is inserted from the treatment instrument insertion port 9, passed through the treatment instrument insertion channel, not shown, and protruded from an opening for treatment instrument (not shown) formed on the distal-end constituting portion 6.

The suction button 12 is an operation member to be used to suck mucus and the like adhered to the distal end of the distal-end constituting portion 6 and to suck the ultrasound medium in the balloon. The gas/liquid feeding button 13 is an operation member to be used to feed gas or liquid to the opening of the gas/liquid feeding unit 23 provided in the distal-end constituting portion 6. The plurality of remote switches 14 include a plurality of operation members for turning on and off control signals (for example, control signals for achieving functions such as stopping of an image, recording of an image, switching of the observation light, etc.) from a control unit and a video processor, neither of them is shown, Note that the configuration for achieving the working associated with the suction operation, the gas feeding operation, and the liquid feeding operation is assumed to be the general one to be applied to a conventional endoscope, and detailed description thereof will be omitted. In addition, the plurality of remote switches 14 are assigned with various functions arbitrarily by setting of the control unit or the video processor, neither of them is shown.

The universal cord 4 is a cord extended from the operation portion 3. The universal cord 4 includes, at the distal end thereof, an endoscope connector 5. Inside the universal cord 4, the image pickup signal line, etc., (not shown), the image pickup control signal line (not shown) as well as the optical fiber cable, and the gas/liquid feeding conduit 23c, not shown, etc., are inserted through. The image pickup signal line is extended from the image pickup unit 21, the image pickup control signal line connects the image pickup unit 21 with the control unit and the video processor, neither of them is shown, and the optical fiber cable connects between the light source apparatus, not shown, and the illumination unit.

The endoscope connector 5 is connected to the distal end of the universal cord 4. The endoscope connector 5 includes a light source connector 5a, a video connector 5b, an ultrasound connector 5c, a liquid feeding pipe 5d, and the like.

The light source connector 5a is a connection terminal that is connected to the light source apparatus, not shown. The video connector 5b is a connection terminal that is connected to the video processor, not shown, through a scope cable, not shown. The ultrasound connector 5c is a connection terminal that is connected to an ultrasound observation control apparatus, not shown, through an ultrasound connection cable, not shown. The liquid feeding pipe 5d is a connection pipe that is connected to a liquid feeding tank, not shown, through a liquid feeding tube, not shown. The liquid feeding pipe 5d is connected to the gas/liquid feeding conduit 23c (not shown in FIG. 1, see FIG. 2, etc., to be described later) inside the light source connector 5a. With such a configuration, the liquid in the liquid feeding tank passes through the liquid feeding tube, the liquid feeding pipe 5d, and the gas/liquid feeding conduit 23c, and ejected from a fluid supply nozzle of the gas/liquid feeding unit 23 provided in the distal-end constituting portion 6 toward a predetermined direction.

Note that the light emitted from the light source apparatus, not shown, is incident on the light source connector 5a. The light incident on the light source connector 5a is transmitted by the optical fiber cable inserted through and disposed insides of the universal cord 4, the operation portion 3, and the insertion portion 2 (flexible tube portion 8), to be emitted from an illumination window 22a (see FIG. 4, etc., to be described later) on the distal-end constituting portion 6.

In addition, the video processor, not shown, is connected to the video connector 5b, through the scope cable, not shown, and electrically connected to the image pickup unit 21 in the distal-end constituting portion 6 through the image pickup cable 21d (see FIG. 2, etc.) that is inserted through and disposed insides of the universal cord 4, the operation portion 3, and the insertion portion 2 (flexible tube portion 8). Furthermore, the video processor is electrically connected to an image display apparatus, not shown, through a video cable, not shown. With such a configuration, the image signal obtained by using the image pickup unit 21 is transmitted to the video processor in which the image signal is subjected to various kinds of predetermined signal processing. Thereafter, the image signal is transmitted to the image display apparatus, not shown, to be visually displayed, as an observation image, on the display screen of the image display apparatus.

The ultrasound observation control apparatus, not shown, is connected to the ultrasound connector 5c through the ultrasound connection cable, not shown, and electrically connected to the ultrasound probe 20 in the distal-end constituting portion 6, through the ultrasound connection line (not shown) inserted through and disposed in the insides of the universal cord 4, the operation portion 3, and the insertion portion 2 (flexible tube portion 8). Other configurations are substantially the same as those of a conventional endoscope.

Figure 2:
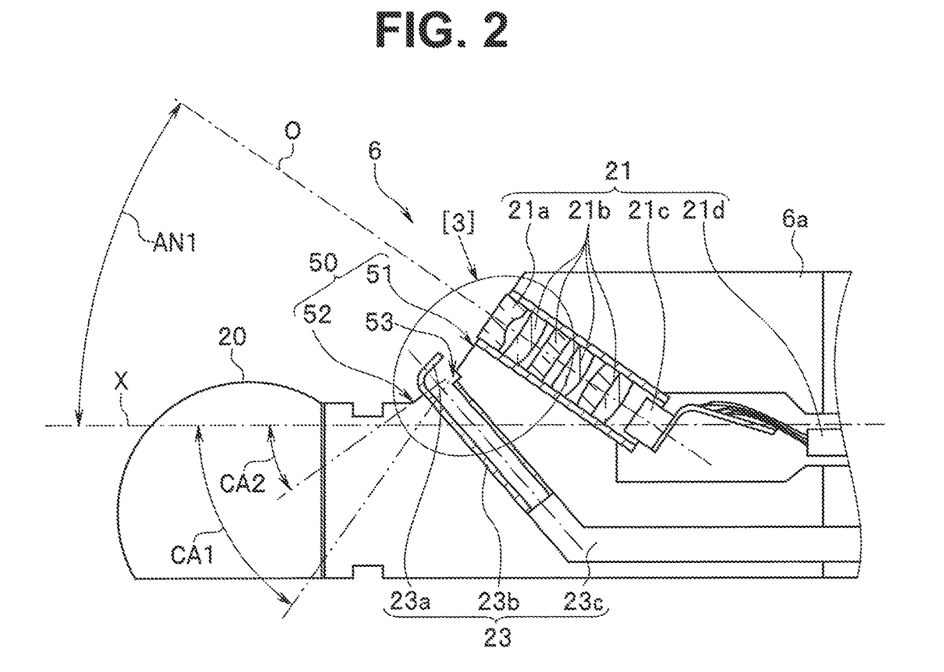
FIG. 2 is a view showing arrangement positions of an image pickup unit and a gas/liquid feeding unit that are disposed in a distal-end constituting portion of the endoscope according to the first embodiment of the present invention.
Figure 3:
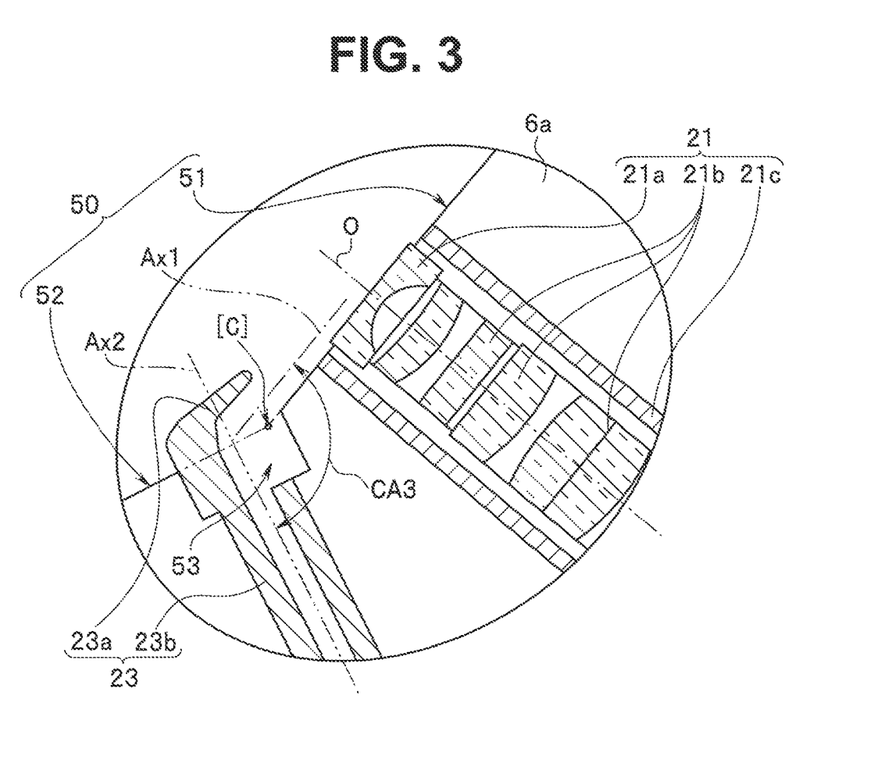
FIG. 3 is a main-part enlarged cross-sectional view of the part indicated by the arrow with the reference sign [3] in FIG. 2.

Next, description will be made on the configuration of the distal-end constituting portion of the endoscope according to the first embodiment of the present invention with reference to FIGS. 2 to 6. FIGS. 2 to 6 are views simply showing the distal-end constituting portion of the endoscope according to the first embodiment of the present invention. Among these drawings, FIG. 2 is a view showing arrangement positions of the image pickup unit and the gas/liquid feeding unit that are disposed in the distal-end constituting portion of the endoscope according to the present embodiment. FIG. 3 is a main-part enlarged cross-sectional view of the part indicated by the arrow with the reference sign [3] in FIG. 2. Note that FIGS. 2 and 3 only show the image pickup unit 21 and the gas/liquid feeding unit 23, in particular, among the plurality of constituting units disposed in the distal-end constituting portion of the endoscope according the present embodiment, and illustrations of other constituting members are omitted.

Figure 4:
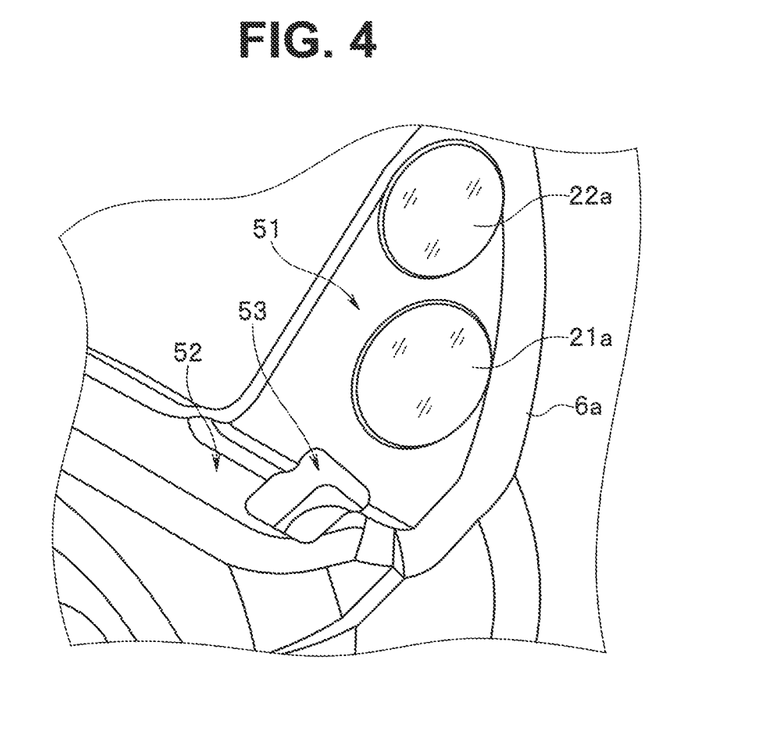
FIG. 4 is an enlarged perspective view of a part of a distal end surface of the distal-end constituting portion of the endoscope according to the first embodiment of the present invention, when viewed from a front diagonal direction.
Figure 5:
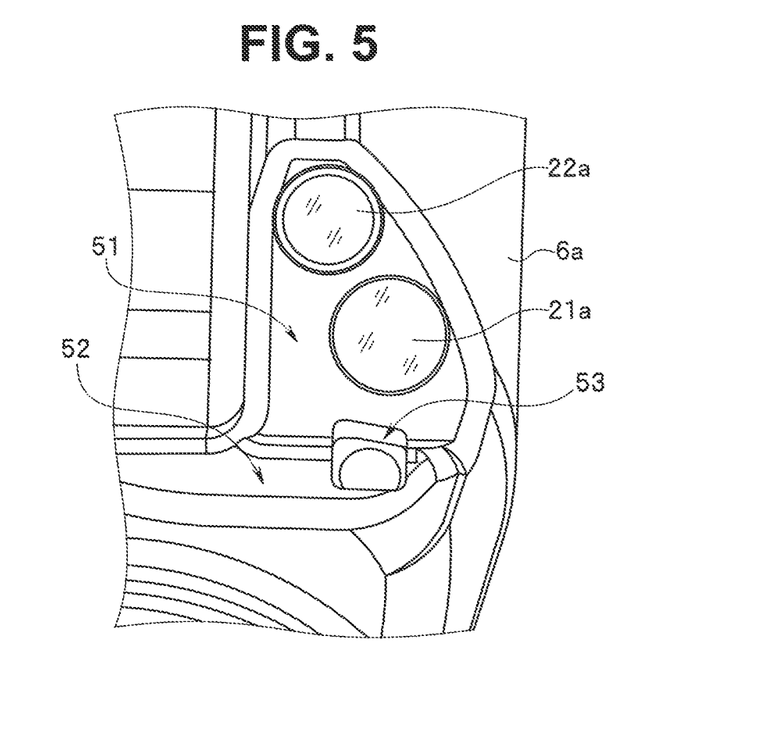
FIG. 5 is an enlarged plan view of a part of the distal end surface of the distal-end constituting portion of the endoscope according to the first embodiment of the present invention, when viewed from the front.
Figure 6:
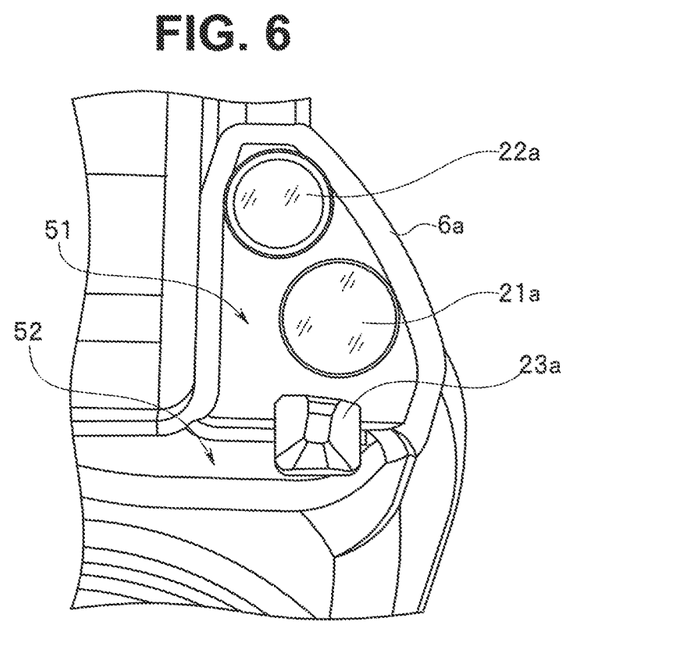
FIG. 6 is a view showing a state where an ejection portion of a fluid supply nozzle is arranged on the distal end surface of the distal-end constituting portion shown in FIG. 4.

In addition, FIGS. 4 and 5 are main-part enlarged views showing, in an enlarged manner, a part of the distal end surface of the distal-end constituting portion of the endoscope according to the present embodiment. Of these drawings, FIG. 4 is an enlarged perspective view of the distal end surface of the distal-end constituting portion, when viewed from the front diagonal direction. FIG. 5 is an enlarged plan view of the distal end surface of the distal-end constituting portion, when viewed from the position facing the distal end surface. Note that, in FIGS. 4 and 5, illustration of the ejection portion of the fluid supply nozzle is omitted in order to show a fluid supply opening formed on the distal end surface of the distal-end constituting portion. In addition, FIG. 6 shows the ejection portion of the fluid supply nozzle on the distal end surface in the state shown in FIG. 4.

The basic configuration of the distal-end constituting portion 6 of the endoscope according to the present embodiment is substantially the same as a basic configuration of a distal end constituting portion of a conventional oblique-viewing ultrasound endoscope. Therefore, FIGS. 2 and 3 only show the main configuration representing the characteristic points of the present embodiment, and illustration of the same configurations as those in a conventional endoscope is omitted.

Among the respective constituting units provided in the distal-end constituting portion 6, the configurations of the image pickup unit 21, the illumination unit, and the gas/liquid feeding unit 23 will be briefly described below.

The image pickup unit 21 is a constituting unit for picking up an optical image of an observation object. The image pickup unit 21, as shown in FIG. 2, etc., is constituted of an observation window 21a, an image pickup optical system 21b, an image pickup device 21c, an image pickup cable 21d, etc.

The observation window 21a is provided so as to cover an opening through which the light flux from the observation object in the subject enters the inside of the distal-end constituting portion 6. The observation window 21a is made of a transparent member such as a glass. The observation window 21a is provided in a predetermined region of the distal end surface of the distal-end constituting portion 6 (detailed later).

The observation window 21a has a field of view direction that intersects the longitudinal axis (see the one-dot chain line indicated by the reference sign X in FIG. 2) of the insertion portion 2. The field of view direction of the observation window 21a corresponds to the optical axis O of the image pickup optical system 21b (hereinafter, referred to as the image pickup optical axis). In other words, the arrangement of the image pickup unit 21 in the distal-end constituting portion 6 is set such that the image pickup optical axis O intersects the longitudinal axis X of the insertion portion 2.

Furthermore, in this case, the observation window 21a is arranged such that the field of view direction (image pickup optical axis O) thereof intersects the longitudinal axis X at an acute angle (see the reference sign AN1 in FIG. 2). In other words, such an arrangement of the observation window 21a indicates that the endoscope 1 according to the present embodiment is an oblique-viewing endoscope in which the image pickup unit 21 is configured to pick up an image in the field of view region in the front diagonal direction.

The image pickup optical system 21b is constituted of a plurality of optical lenses and the like, and the plurality of optical lenses are configured to form an optical image of the observation object on a predetermined image-forming surface (the light-receiving surface of the image pickup device 21c). Note that the observation window 21a may be included in the image pickup optical system 21b.

The image pickup device 21c is an electronic part that receives the optical image of the observation object, which is formed by the image pickup optical system 21b, performs photoelectric conversion processing on the optical image, and generates image data of the observation object.

The image pickup cable 21d is formed by bundling various signal lines extended from the image pickup device 21c. The image pickup cable 21d includes, for example, the image pickup signal line, the image pickup control signal line, etc. The image pickup signal line is configured to transmit the output signal from the image pickup device 21c to the control unit and the video processor, neither of them is shown. The image pickup control signal line is configured to transmit the control signals from the control unit and the video processor, neither of them is shown.

The illumination unit is a constituting unit for supplying illumination light to the observation object. The illumination unit includes the illumination window 22a (not shown in FIGS. 2 and 3, see FIGS. 4 to 6) as a supply unit arranged on the distal end surface of the distal-end constituting portion 6, the illumination lens, not shown, and the optical fiber cable or a light-emitting element such as an LED. Note that the illumination unit is a constituting unit not directly related to the present embodiment. Therefore, illustration of the illumination unit is omitted in FIGS. 2 and 3. In addition, FIGS. 4 to 6 show only the illumination window 22a, and illustration of the internal configuration of the illumination unit is omitted.

The gas/liquid feeding unit 23 is a constituting unit for supplying a fluid (liquid or gas) toward the front faces of the observation window 21a and the illumination window 22a. The gas/liquid feeding unit 23 includes the fluid supply nozzle as a supply unit, the gas/liquid feeding conduit 23c, and the like.

The fluid supply nozzle includes an ejection portion 23a formed at the distal end of the nozzle, and a conduit portion 23b formed on the upstream side of the ejection portion 23a. The conduit portion 23b is connected to the distal end of the gas/liquid feeding conduit 23c. With such a configuration, the fluid ejected from the ejection portion 23a of the fluid supply nozzle of the gas/liquid feeding unit 23 is ejected toward the observation window 21a and the illumination window 22a, to remove the dirt adhered to the front faces of the observation window 21a and the illumination window 22a.

Note that it is assumed that the basic configurations of the illumination unit and the gas/liquid feeding unit 23 are the same as those applied to a conventional endoscope. Accordingly, the descriptions and illustrations of the detailed configurations of the constituting units which are the same as those applied to the conventional endoscope will be omitted.

Next, description will be made below on the characteristic points of the external shape of the distal-end constituting portion 6 according to the present embodiment. A distal end surface 50 constitutes a part of the surface of the distal-end constituting portion 6 of the present embodiment and is formed so as to face the region in front of the distal-end constituting portion 6. As shown in FIGS. 2 to 6, the distal end surface 50, as a whole, is formed by a plane having an inclination with respect to the longitudinal axis X of the insertion portion 2.

In detail, the distal end surface 50 of the distal-end constituting portion 6 of the present embodiment includes a first flat surface 51 and the second flat surface 52. In this case, the first flat surface 51 has a first intersection angle CA1 (see FIG. 2) with respect to the longitudinal axis X. On the first flat surface 51, the observation window 21a and the illumination window 22a are arranged (with regard to the illumination window 22a, see FIGS. 4 to 6).

In addition, the second flat surface 52 has a second intersection angle CA2 (see FIG. 2) with respect to the longitudinal axis X. The second intersection angle CA2 is smaller than the first intersection angle CA1 (CA1>CA2). The second flat surface 52 is provided on the distal end side with respect to the first flat surface 51. On the second flat surface 52, the ejection portion 23a of the fluid supply nozzle is disposed.

As shown in FIG. 3, the fluid supply nozzle is formed such that a center axis Ax1 of the ejection portion 23a and a center axis Ax2 of the conduit portion 23b intersect with each other at a predetermined angle larger than the angle of 0 degree. The predetermined angle is an obtuse angle (see the reference sign CA3 in FIG. 3). Therefore, with such a configuration, a part of the ejection portion 23a (for example, the ejection opening located at the distal-most part of the ejection portion 23a) is arranged so as to face the first flat surface 51.

Furthermore, a recess portion 53 is formed in a region which is in the vicinity of the site where a part of the ejection portion 23a (for example, the ejection opening) is arranged and which includes the boundary part (see the part indicated by the reference sign [C] in FIG. 3) between the first flat surface 51 and the second flat surface 52.

According to the first embodiment configured as described above, the endoscope 1, what is called an oblique-viewing endoscope, is configured such that the field of view direction of the observation window 21a of the image pickup unit 21 intersects the longitudinal axis (insertion axis) X at the acute angle AN1. The distal-end constituting portion 6, which is provided at the distal end of the insertion portion 2 of the endoscope 1, includes, on the distal end surface 50 as a part of the surface thereof, the first flat surface 51 and the second flat surface 52.

In this case, the first flat surface 51 is formed so as to have the intersection angle CA1 with respect to the longitudinal axis X. The second flat surface 52 is formed so as to have the second intersection angle CA2 with respect to the longitudinal axis X. The second intersection angle CA2 is smaller than the first intersection angle CA1 (CA1>CA2). The second flat surface 52 is provided on the distal end side with respect to the first flat surface 51.

In such a configuration, on the first flat surface 51, the observation window 21a and the illumination window 22a are arranged. On the second flat surface 52, the fluid supply nozzle is arranged.

With such a configuration, the distal-end constituting portion 6 of the endoscope 1 according to the present embodiment includes the first flat surface 51 which allows the field of view direction of the observation window 21a to be close to that of an observation window in a front-viewing endoscope, and the second flat surface 52 formed directed toward more lateral side than the first flat surface 51. With such a configuration, the second flat surface 52 can ensure a sufficient large area for arranging the fluid supply nozzle.

In addition, the field of view direction of the observation window 21a is configured to be close to that of an observation window in a front-viewing endoscope, which can contribute to the improvement of the insertion performance. Furthermore, the fluid supply nozzle can be arranged efficiently, which prevents the impairment of the performance of the gas/liquid feeding unit 23 for cleaning the observation window 21a. Thus, the configuration can contribute to the improvement of the image pickup performance.

The endoscope 1 according to the present embodiment can thus achieve both the effective, efficient, and appropriate arrangement of the observation window 21a, the fluid supply nozzle, and the like that are arranged on the distal end surface 50 of the distal-end constituting portion 6 and the improvement of the insertion performance of the insertion portion 2.

Furthermore, the image pickup unit 21 and the gas/liquid feeding unit 23 that are arranged in the distal-end constituting portion 6 can be arranged such that the respective axes (the image pickup optical axis O, the center axis Ax2) extend in the directions not interfering with each other inside the distal-end constituting portion 6 (see FIG. 2). Therefore, such an arrangement can provide also an effect that the assembling is easy in incorporating the image pickup unit 21, the gas/liquid feeding unit 23, and the like into the distal-end constituting portion 6. The configuration according to the present embodiment can thus contribute to the simplification of the manufacturing process of the distal-end constituting portion 6 of the endoscope 1.

The above-described first embodiment shows the configuration example in which the recess portion 53 is formed in the region which is in the vicinity of the site where a part of the ejection portion 23a (for example, the ejection opening) is arranged and which includes the boundary part [C] (see FIG. 3) between the first flat surface 51 and the second flat surface 52. However, the recess portion 53 does not necessarily have to be provided.

If the recess portion 53 is omitted, for example, it is preferable to arrange the site where a part (the ejection opening, for example) of the ejection portion 23a is arranged within the range of the second flat surface 52. Also in such a configuration, it is preferable that a part (the ejection opening, for example) of the ejection portion 23a is arranged so as to face the first flat surface 51.

In addition, the above-described first embodiment shows the configuration example in which the second flat surface 52 is provided on the distal end side with respect to the first flat surface 51. However, the arrangement of the second flat surface 52 is not limited to the configuration. For example, the second flat surface 52 may be provided on the proximal end side with respect to the first flat surface 51.

Furthermore, the above-described first embodiment shows the configuration example in which the fluid supply nozzle, as the supply unit of the fluid, is arranged on the second flat surface 52. However, the supply unit arranged on the second flat surface 52 is not limited to the fluid supply nozzle. For example, the illumination window, as the supply unit of the illumination light, may be provided on the second flat surface 52.

Figure 7:
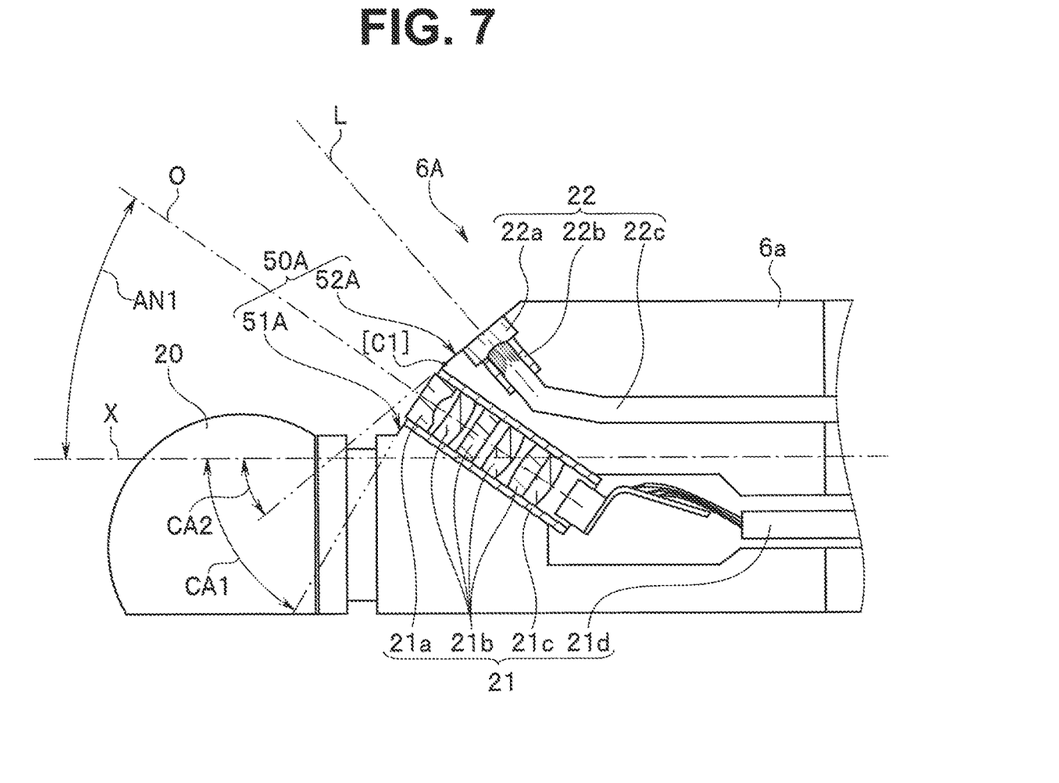
FIG. 7 is a view showing arrangement positions of an image pickup unit and an illumination unit that are disposed in a distal-end constituting portion of an endoscope according to a second embodiment of the present invention.

Next, description will be made on a distal-end constituting portion of an endoscope according to a second embodiment of the present invention. FIG. 7 is a view showing arrangement positions of an image pickup unit and an illumination light that are disposed in the distal-end constituting portion of the endoscope according to the second embodiment of the present invention.

A distal-end constituting portion 6A according to the present embodiment basically has a configuration substantially the same as that of the distal-end constituting portion in the above-described first embodiment. Therefore, the same constituent elements as those in the first embodiment are attached with the same reference signs and the description thereof will be omitted. Only different constituent elements will be described below.

A distal end surface 50A of the distal-end constituting portion 6A according to the present embodiment is configured such that a second flat surface 52A is provided on the proximal end side with respect to a first flat surface 51A. In addition, in the distal-end constituting portion 6A according to the present embodiment, the observation window 21a is provided on the first flat surface 51A and the illumination window 22a of the illumination unit 22 is provided on the second flat surface 52A.

In the present embodiment, as shown in FIG. 7, the illumination unit 22 includes the illumination window 22a, an illumination lens 22b, an optical fiber cable 22c, etc. Note that the illumination unit may be configured such that a light-emitting element such as an LED is used instead of the optical fiber cable 22c.

The first flat surface 51A has a first intersection angle CA1 with respect to the longitudinal axis X. The second flat surface 52A has a second intersection angle CA2 with respect to the longitudinal axis X. The second intersection angle CA2 is smaller than the first intersection angle CA1 (CA1>CA2). In this configuration, a boundary part [C1] between the first flat surface 51A and the second flat surface 52A intersect the longitudinal axis X at an angle larger than the angle of 180 degrees.

Note that, in such a configuration, the optical axis L of the illumination window 22a (hereinafter, referred to as illumination optical axis) and the image pickup optical axis O extend in directions apart from each other. Therefore, in this case, there is a possibility that the image pickup region of the image pickup unit 21 cannot be fully irradiated with the illumination light applied from the illumination window 22a of the illumination unit 22.

Generally, it is preferable that the irradiation range of the illumination light applied from the illumination window 22a of the illumination unit 22 covers the entire image pickup region of the image pickup unit 21. Therefore, in the case of employing the configuration of the present embodiment, it is preferable to set such that the illumination optical axis L and the image pickup optical axis O are substantially parallel to each other, in other words, the irradiation range of the illumination light covers the image pickup region, by devising the optical characteristic of the illumination window 22a, for example.

In the present embodiment, although the arrangement of the gas/liquid feeding unit is not specifically mentioned, the fluid supply nozzle of the gas/liquid feeding unit may be arranged on the first flat surface 51A, for example, such that the ejection direction of the fluid supply nozzle is directed toward the front faces of the observation window 21a and the illumination window 22a.

The second embodiment configured as described above includes the first flat surface 51A that allows the field of view direction of the observation window 21a to be close to that of an observation window in a front-viewing endoscope, and the second flat surface 52A formed directed toward more lateral side than the first flat surface 51A. With such a configuration, the second flat surface 52A can ensure a sufficiently large area for arranging the illumination window 22a.

Figure 8:
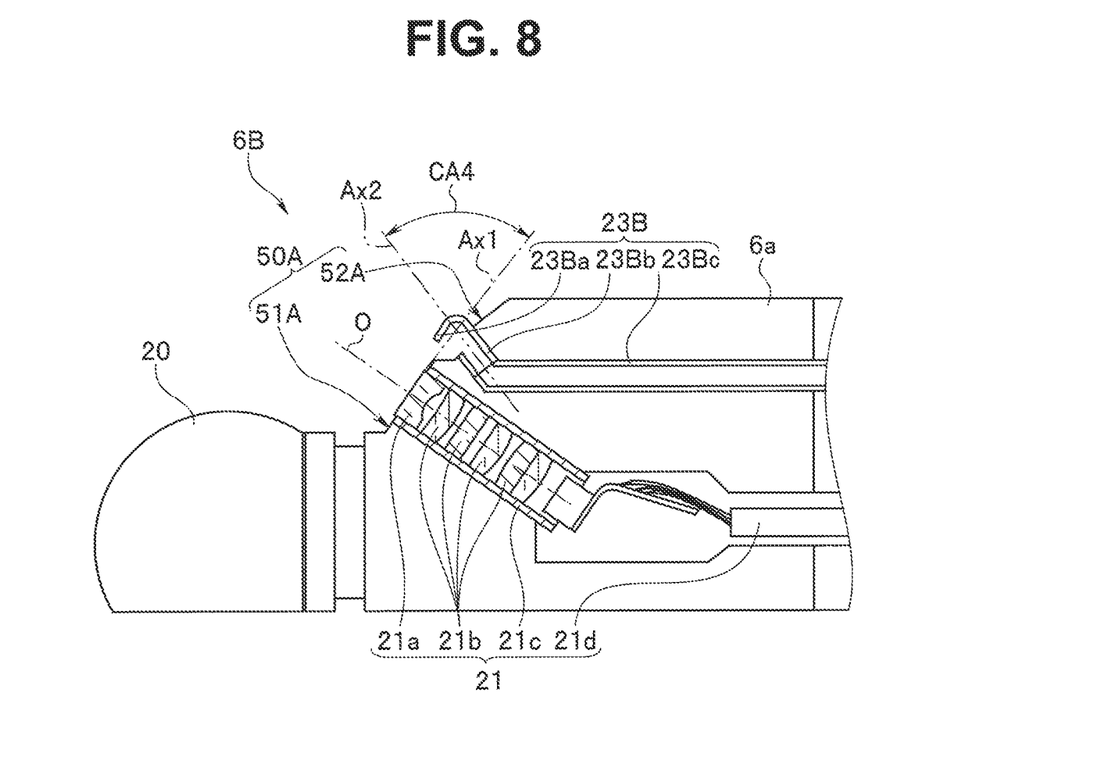
FIG. 8 is a view showing arrangement positions of an image pickup unit and a gas/liquid feeding unit that are disposed in a distal-end constituting portion of an endoscope according to a third embodiment of the present invention.

Next, description will be made on a distal-end constituting portion of an endoscope according to a third embodiment of the present invention. FIG. 8 is a view showing arrangement positions of an image pickup unit and a gas/liquid feeding unit that are disposed in a distal-end constituting portion of the endoscope according to the third embodiment of the present invention.

A distal-end constituting portion 6B according to the present embodiment basically has a configuration substantially the same as that of the distal-end constituting portion in the above-described second embodiment. Therefore, the same constituent elements as those in the second embodiment are attached with the same reference signs and the description thereof will be omitted. Only different constituent elements will be described below.

A distal end surface 50A of the distal-end constituting portion 6B according to the present embodiment is configured such that the second flat surface 52A is provided on the proximal end side with respect to the first flat surface 51A, similarly as in the above-described second embodiment. In addition, in the distal-end constituting portion 6B according to the present embodiment, the observation window 21a is provided on the first flat surface 51A and the fluid supply nozzle is provided on the second flat surface 52A.

A gas/liquid feeding unit 23B according to the present embodiment includes an ejection portion 23Ba, a conduit portion 23Bb, a gas/liquid feeding conduit 23Bc, etc.

In such a configuration, a center axis Ax2 of the conduit portion 23Bb of the fluid supply nozzle and the image pickup optical axis O extend in directions apart from each other. In addition, a center axis Ax1 of the ejection portion 23Ba of the fluid supply nozzle extends in the direction apart from the first flat surface 51A. Therefore, in this case, there is a possibility that the fluid ejected from the ejection portion 23Ba of the fluid supply nozzle is not sufficiently ejected to the front face of the observation window 21a of the image pickup unit 21.

Therefore, in the case of employing the configuration of the present embodiment, the fluid supply nozzle is formed such that the center axis Ax1 of the ejection portion 23Ba intersects the center axis Ax2 of the conduit portion 23Bb at a predetermined angle which is larger than the angle of 0 degree. The predetermined angle is an acute angle (see the reference sign CA4 in FIG. 8). With such a configuration, a part of the ejection portion 23Ba (the ejection opening at the distal-most part of the ejection portion 23Ba) is arranged so as to face the first flat surface 51A. With such a configuration, the fluid ejected from the ejection portion 23Ba of the fluid supply nozzle is ejected sufficiently to the front face of the observation window 21a of the image pickup unit 21.

In the present embodiment, although the arrangement of the illumination unit is not specifically mentioned, the illumination window of the illumination unit may be arranged on the second flat surface 52A, for example, such that the ejection direction of the fluid supply nozzle is directed toward the front faces of the observation window 21a and the illumination window 22a.

The third embodiment as described above includes the first flat surface 51A that allows the field of view direction of the observation window 21a to be close to that of an observation window in a front-viewing endoscope, and the second flat surface 52A formed directed toward more lateral side than the first flat surface 51A. With such a configuration, the second flat surface 52A can ensure a sufficiently large area for arranging the fluid supply nozzle.

Note that the distal-end constituting portion of the endoscope according to each of the above-described embodiments is configured by incorporating a plurality of various constituting units (image pickup unit, illumination unit, gas/liquid feeding unit, etc.). Therefore, the distal-end constituting portion, as a single unit, is a relatively expensive constituting unit. Therefore, in a case of what is called a single-use endoscope of a type to be disposed (discarded) after a single usage, for example, it can be considered that only the distal-end constituting portion is configured to be replaceable, and to be reused. Accordingly, only the distal-end constituting portion is possibly distributed as a single constituting unit.

The present invention is not limited to the above-described embodiments, and it goes without saying that various modifications and applications can be implemented without departing from the gist of the invention. Furthermore, the above embodiments include inventions at various stages, and various inventions can be extracted by appropriate combinations in the plural disclosed components. For example, even when some of the components are removed from all the components shown in the one embodiment described above, a configuration from which the components are eliminated can be extracted as an invention insofar as the configuration can solve the problem to be solved by the invention and attain the effects of the invention. Furthermore, components over different embodiments may be combined as appropriate. The invention is not limited by the specific embodiments except as limited by appended claims.

What is claimed is:

1. A distal-end portion for use with an endoscope, the distal-end portion comprising:
    a base member comprising:
        a first surface having a first angle relative to a longitudinal axis of the base member the first surface facing distally, and the first angle being non-perpendicular relative to the longitudinal axis; and
        a second surface having a second angle relative to the longitudinal axis, the second angle being smaller than the first angle, the second surface facing distally, and the second angle being non-perpendicular relative to the longitudinal axis,
    an observation window arranged on the first surface, the observation window having a field of view direction that intersects the longitudinal axis; and
    a supply unit arranged on the second surface wherein the supply unit is a fluid supply nozzle configured to supply fluid across the first surface.

2. The distal end portion according to claim 1, wherein:
    the first angle is a smaller of two supplementary angles of the first surface relative to the longitudinal axis; and
    the second angle is a smaller of two supplementary angles of the second surface relative to the longitudinal axis.

3. The distal-end portion according to claim 1, wherein the supply unit is an illumination unit configured to supply light.

4. The distal-end portion according to claim 1, wherein the fluid supply nozzle comprises,
    an ejection surface configured to eject the fluid in a first direction; and
    a conduit provided in the base member, and the conduit communicating with the ejection surface, and the conduit extending in a second direction intersecting with the first direction.

5. The distal-end portion according to claim 4, wherein the second surface is provided distally relative to the first surface, and
    the first direction intersects with the second direction at an obtuse angle.

6. The distal-end portion according to claim 4, wherein the second surface is provided proximally relative to the first surface, and
    the first direction intersects with the second direction at an acute angle.

7. The distal-end portion according to claim 4, wherein a part of the ejection surface is protruded from the second surface and arranged so as to face the first surface.

8. The distal-end portion according to claim 7, wherein
    one or more of the first surface and the second surface include a recessed surface recessed from one or more of the first surface and the second surface, and
    the ejection surface is provided at the recessed surface.

9. The distal-end portion according to claim 1, wherein an optical axis direction of the observation window intersects the longitudinal axis at an acute angle; and
    the acute angle is a smaller of two supplementary angles of the optical axis direction relative to the longitudinal axis.

10. The distal-end portion according to claim 1, wherein the second surface is provided distally relative to the first surface in a longitudinal axis direction.

11. The distal-end portion according to claim 1, wherein the second surface is provided proximally relative to the first surface in a longitudinal axis direction.

12. The distal-end portion according to claim 1, wherein one or more of the first surface and the second surface is a flat surface.

13. The distal-end portion according to claim 1, further comprising an illumination unit arranged on one or more of the first surface and the second surface, the illumination unit configured to supply light; and
    wherein the illumination unit includes an illumination window on the first surface.

14. The distal-end portion according to claim 13, wherein the supply unit is configured to supply fluid toward one or more of the observation window and the illumination window.

15. The distal-end portion according to claim 1, wherein the fluid supply nozzle configured to supply fluid toward the observation window.

16. An insertion portion comprising:
    the distal-end portion according to claim 1, and
    an ultrasound probe provided distally relative to the distal-end portion.

17. An endoscope comprising:
    an insertion portion configured to be inserted into a subject, the insertion portion comprising:
    the distal-end portion according to claim 1, the distal-end portion provided at a distal end of the insertion portion.

18. The distal-end portion according to claim 1, wherein a plane including the second surface intersects with the longitudinal axis distally relative to the second surface.

19. The distal-end portion according to claim 1, wherein an entirety of the second surface is located at a different radial position than an entirety of the first surface.

* * * * *